United States Patent [19]

Grisar et al.

[11] 4,037,962
[45] July 26, 1977

[54] APPARATUS FOR THE SPECTRAL ANALYSIS OF MATERIALS

[75] Inventors: Ulrich Grisar; Wilhelm Berstermann, both of Georgsmarienhutte, Germany

[73] Assignee: Klöckner-Werke AG, Duisburg, Germany

[21] Appl. No.: 665,771

[22] Filed: Mar. 10, 1976

[30] Foreign Application Priority Data

Mar. 26, 1975 Germany .............................. 2513345

[51] Int. Cl.² .............................................. G01J 3/30
[52] U.S. Cl. ......................................... 356/86; 356/98
[58] Field of Search ...................... 356/76, 77, 79, 81, 356/82, 86, 98, 80; 250/227

[56] References Cited

U.S. PATENT DOCUMENTS

| | | | |
|---|---|---|---|
| 2,723,590 | 11/1955 | Berthold | 356/86 |
| 2,837,959 | 6/1958 | Saunderson et al. | 356/80 |
| 3,645,628 | 2/1972 | Bojic et al. | 356/86 |
| 3,909,133 | 9/1975 | Hobson et al. | 356/86 |
| 3,942,892 | 3/1976 | Ambrose et al. | 250/227 X |

Primary Examiner—F. L. Evans
Attorney, Agent, or Firm—Michael J. Striker

[57] ABSTRACT

An apparatus for spectroscopically analyzing the composition of a workpiece comprises a support on which is mounted a sleeve having an open end engageable with the surface of the workpiece and formed with a laterally open cutout. An electrode is mounted on the support and has an electrode tip limitedly displaceable in the sleeve adjacent the open end thereof. A laterally extending screw is engaged between an insulating tube constituting part of the support and the electrode and serves to fix the electrode in the sleeve with the electrode tip spaced inwardly of the open end of the sleeve. A power supply is connected to the electrode for sparking between the surface of the workpiece and the tip when the two are spaced apart and the open end of the sleeve abuts the surface. A lens on the support is directed through the cutout at the space between the electrode tip and the workpiece surface and cooperates with a primary slit to transmit into the support the light of a spark in the space between the electrode tip and the workpiece surface. A Rowland grating having a plurality of secondary slits is provided in the support for breaking the light received from the lens and primary slit down into an analyzable spectrum.

10 Claims, 3 Drawing Figures

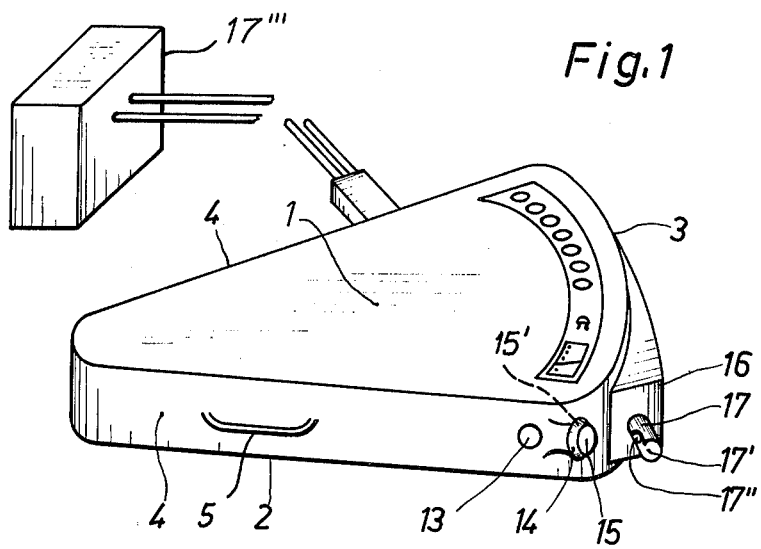
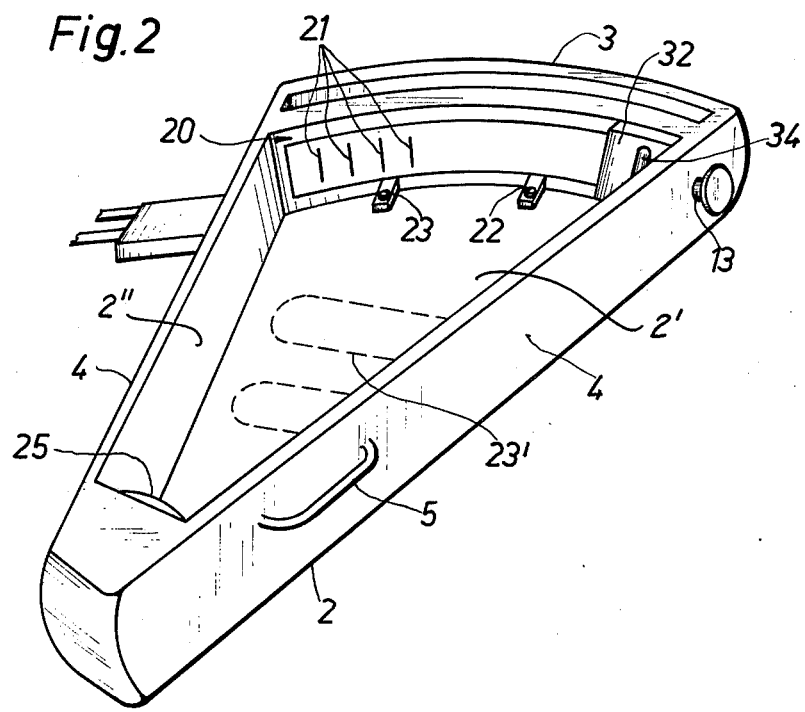

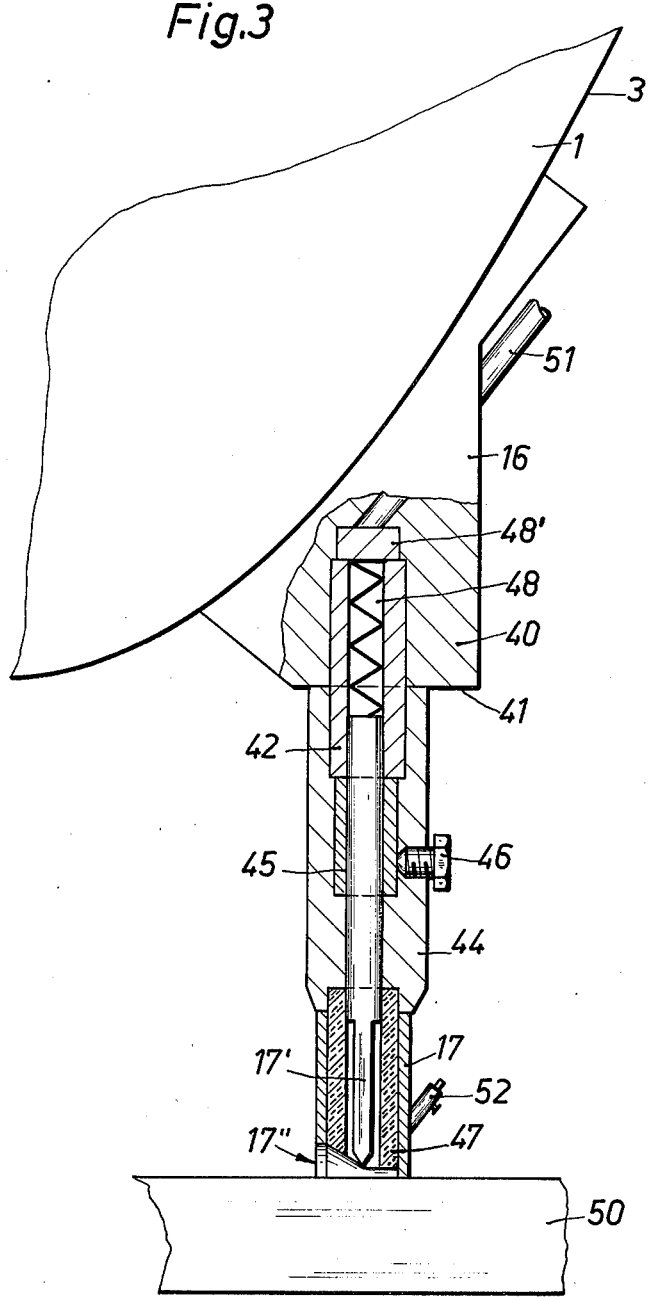

APPARATUS FOR THE SPECTRAL ANALYSIS OF MATERIALS

CROSS-REFERENCE TO RELATED APPLICATIONS:

This application is related to the copending applications Ser. Nos. 665,770 and 665,772-665,774 all filed Mar. 10, 1976.

BACKGROUND OF THE INVENTION

The invention relates generally to an arrangement for the spectral analysis of substances. Of particular interest to the invention is an arrangement for use in the determination of the alloying components of metals by spectral analysis.

A known arrangement of this type includes a primary slit and a concave diffraction grating as well as a series of secondary slits which are arranged on a circle. The positions of the secondary slits correspond to the spectral lines which are to be investigated. In operation, a spark discharge is generated between a suitable electrode and a metallic sample to be investigated. The radiation thus produced is directed onto the diffraction grating via the primary slit and the diffraction grating then produces a spectrum of series of spectral lines which are characteristic of the sample being investigated. The intensity of the lines is measured with photographic detectors. The latter generate signals which provide a measure of the proportions of the different elements in the sample.

The spectrum-forming properties of concave gratings are defined by their astigmatism.

In a plane transverse to the lines or rulings of a grating, the image locations lie on a circle, the so-called Rowland circle, when the primary slit likewise lies on this circle. The circle is tangent to the surface of the grating at the center of the concave grating and the diameter of the circle equals the radius of curvature of the concave grating. In a plane parallel to the lines or rulings of the gratings, the image points are not clearly formed on the circle and the primary slit must be adjusted so as to be precisely parallel to the lines or rulings of the grating if the resolving power of the grating is not to be reduced.

The currently known spectrometers for determining the compositions of metallic alloys and similar materials, also known as quantometers, and which operate with concave gratings have large dimensions. Accordingly, they are constructed in the form of stationary apparatus for laboratory operation. The large dimensions are, above all, a result of the fact that circle diameters of less than about 1 meter have not been used heretofore. The reason resides in the previously held conception that, if a circle diameter of less than about 1 meter were used, the adjustment of the primary slit would be either impossible or else so complicated that it would only be possible to operate in scientific institutes with suitable specialists.

The adjustment of the primary slit must be effected very carefully and with great precision. In order to accomplish this, the primary slit in the known spectrometers is positioned, for example, on a swiveling arm which is supported on a pivot in the vicinity of the entry window provided for the purpose of permitting the radiation from the spark discharge to travel to the grating for resolution into a spectrum. On the other hand, the primary slit may be mounted so as to be linearly displaceable with a spindle. For the small corrections which are necessary, the large radius of curvature of the Rowland circle makes it possible, as a first approximation, to consider the are in the region of the primary slit as a linear section. The relatively simple adjustment of the slit which thus becomes possible has, however, associated with it the disadvantage of operating satisfactorily only in spectrometers having a grating of long focal length and, concomitantly, a large Rowland circle.

The large dimensions of the known spectrometers which are mounted so as to be stationary generally do not pose a disadvantage for the spectrometers. The reason resides in that a portion of the spectral lines to be investigated lie in the short wavelength ultraviolet range of the spectrum. Since the short wavelength ultraviolet rays are absorbed by air, the spectrometer itself must be evacuated and for this purpose large auxiliary apparatus is required. Thus, the combination of the spectrometer and the auxiliary apparatus would have large dimensions even if the dimensions of the spectrometer were relatively small.

In those cases where it is intended to analyze substances in order to determine alloying components having usable spectral lines which lie in the visible or long wavelength ultraviolet regions, the auxiliary apparatus for the so-called vacuum ultraviolet are not necessary.

Such an "air device" is not as universally applicable as the "vacuum quantometer" since certain elements cable as the "vacuum quantometer" since certain elements cannot be detected. Nevertheless, it offers great advantages in the quality control of materials, both for the producer and the user of the materials. For instance, a producer or a user may be interested in sorting out in a simple manner those bars in a bundle of bars to be delivered which have proportions of alloying components different from the required proportions. However, it is always necessary to bring the individual bars, or discs cut from these bars, to the spectrometer since, as outlined above, the known spectrometers of the type under discussion cannot be transported to the workpiece to be investigated. In particular, it is not possible, for instance, to bring such spectrometers into position above a conveyor belt containing the workpieces to be analyzed so that those workpieces having a composition different from the required or predetermined composition may be registered and sorted out.

One of the earlier-mentioned applications by the same assignee, namely, the application Ser. No. 655,770 filed Mar. 10, 1976, concerns itself with making it possible to select the diameter of the Rowland circle so as to be small while nevertheless permitting a precise adjustment or alignment of the primary slit to be achieved. A spectrometer formed in this manner may be readily constructed as a transportable device when it operates only the visible and near ultraviolet spectral regions.

To achieve these ends, the just-mentioned application discloses a spectrometric device of the Rowland character which, in a preferred form, includes, a housing and wherein a plate provided with the primary slit is movably arranged on the arc of the Rowland circle interiorly of the housing and is mounted so as to be capable of being arrested in any one of a plurality of positions. By virtue of this construction, there is achieved the result that an adjustment or alignment of the primary slit continuously occurs on the circle and parallel thereto. Consequently, it is no longer necessary to select the diameter of the circle to be so large that, as a first approximation, an arc segment thereof may be considered to be a linear section for the purpose of alignment of the primary slit.

In particularly advantageous embodiment of the foregoing application Ser. No. 665,770 filed Mar. 10, 1976, it is proposed that the plate with the primary slit be guided in two grooves which follow the curvature of the Rowland circle and that the plate be capable of being arrested in the grooves. By virtue of this guidance, an adjustment or alignment along the circle may be insured, on the one hand, while it becomes possible, on the other hand, to achieve a mounting of the slit which is not affected by vibrations.

However, the following problem exists here. In order to generate a spark discharge in the known quantometers, the sample under investigation is placed on a Petrey table and stressed. The sample defines a spark gap with the counterelectrode and ignition is effected by generating a large potential difference across the spark gap. The sample here serves as an electrode of the spark gap. The Petrey table is necessary in order that the spark discharge be produced at a predetermined distance from the primary slit since otherwise an exact formation of the image of the spark gap or spark discharge on the diffraction grating is not possible despite a correct alignment of the primary slit.

Although it is possible, in principle, to integrate the Petrey table in the spectrometric device disclosed in the aforementioned application Ser. No. 665,770 filed Mar. 10. 1976, the handiness of the device, as well as its range of applicability, will be limited thereby. For example, in analyzing the bars contained in a bundle of bar stock which has been delivered to a user or which is to be sent out by a manufacturer, it is necessary, for a device provided with a Petrey table, to cut individual samples from the bars and to stress the samples on the Petrey table rather than being able to perform the analysis without these time-consuming procedures.

SUMMARY OF THE INVENTION:

It is an object of the invention to provide an arrangement for the spectral analysis of substances which enables a spark discharge to take place at a predetermined distance from the primary slit without requiring that specimens be removed from the substances to be investigated.

Another object of the invention is to arrange the counterelectrode, which defines the spark gap together with the material to be investigated, in such a manner that a spark discharge will always be generated at a predetermined distance from the primary slit without requiring that specimens be removed from the material under investigation and, further, to provide an arrangement of this character which is of such a nature that the operating personnel may be protected against high-voltage shocks.

These objects, as well as others which will become apparent as the description proceeds, are achieved in accordance with the invention. According to one aspect of the invention, there is provided an arrangement for the spectral analysis of substances, particularly for use in the determination of the composition of metallic alloys and similar materials, which includes a support and a diffraction grating on the support for producing the spectrum characteristic of a sample being investigated. The support has a series of slits thereon which are adjusted to the spectral lines of samples to be investigated. A primary slit on the support serves to direct the radiation derived from a spark discharge involving a sample being investigated onto the grating. An electrode or counterelectrode is provided on the support for the generation of a spark discharge with a sample being investigated and the counterelectrode has a spark-generating tip or end portion arranged to be located proximate to a sample being investigated during the spark discharge. A sleeve or sleeve member surrounds the spark-generating end of the counterelectrode and permits a predetermined distance to be maintained between the spark-generating end of the counterelectrode and a sample under investigation. The sleeve is favorably metallic. The sleeve has an edge portion or edge which is arranged to be located adjacent a sample being investigated during the spark discharge. According to the invention, this edge of the sleeve is provided with a cutout arranged in such a manner that, when the edge of the sleeve is located adjacent a sample being investigated, the sample and the cutout together define a directional opening for directing the radiation derived from the spark discharge to the primary slit.

The arrangement or spectrometric device of the invention may advantageously be of the Rowland character. Thus, the diffraction grating is favorably in the form of a concave grating and the primary slit, as well as the series of secondary slits on the support, are favorably arranged on the Rowland circle.

It has already been mentioned that the invention is particularly interested in a device for the determination of the alloying components of metals by spectral analysis. The invention relates, as will be appreciated, to a spectrometric device having a primary slit, a concave diffraction grating and a series of secondary slits which are arranged on a circle and the positions of which correspond to the spectral lines to be investigated. A suitable counterelectrode is provided and, in operation, a spark discharge is generated between the counterelectrode and a metallic sample to be investigated. The radiation from the spark discharge is directed onto the concave grating via the primary slit and the grating then produces a spectrum or series of spectral lines characteristic of the sample being investigated. The intensity of the lines may be measured with photoelectric detectors, which latter may generate signals providing a measure of the proportions of the different elements in the sample.

The support of the arrangement according to the invention may include a housing and, in accordance with a preferred embodiment of the invention, the objects of the invention are achieved in that the counterelectrode, which forms the spark gap together with the material under investigation, is arranged on the housing of the spectrometric device in a metallic sleeve. The sleeve has a cutout at the edge thereof which, after the spectrometric device or sleeve has been placed on the sample to be investigated, defines with the sample a directional opening for forming an image of the spark discharge at the primary slit, that is, the cutout and the sample together define a directional opening for directing the radiation derived from the spark discharge to the primary slit. By virtue of this construction, there is achieved the result that the spectrometric device need merely be placed on or adjacent to the sample being investigated so that the sleeve contacts the same and that the distance between the sample and the counterelectrode, which together define the spark gap, is then predetermined by means of the sleeve. At the same time, the directional opening fixes the location of the spark discharge so that an image of the latter is formed at the primary slit and, concomitantly, also at the Rowland grating, the formation of the image of the spark discharge being undertaken by means of an optical system.

According to a particularly favorable embodiment of the invention, the counterelectrode is accommodated in an insulating body mounted on the housing of the spectrometric device and extends from the insulating body into the sleeve. The counterelectrode is here arranged in such a manner within the insulating body that it may be arrested in any one of a plurality of positions. By virtue of this construction, the high voltage supplied to the counterelectrode for the spark discharge is kept away from the spectrometric device proper. Moreover, this construction permits an adjustment of the counterelectrode relative to the sleeve to be effected prior to the locking or arresting of the counterelectrode.

In accordance with a further embodiment of the invention, the spacing of the counterelectrode from the plane of the edge of the sleeve is substantially equal to the electrode spacing of the spark gap to be formed by the counterelectrode and a sample to be investigated. Due to this measure, there is achieved the result that the spark gap breakdown always occurs between the counterelectrode and the sample under investigation and not between the counterelectrode and the sleeve. It is, of course, self-understood that here the width of the annular gap between the counterelectrode and the sleeve should be greater than the electrode spacing of the spark gap or the spacing between the counterelectrode and the plane of the edge of the sleeve.

According to another advantageous embodiment of the invention, the sleeve is provided with a terminal for connection to a protective circuit which isolates the spark gap, that is, prevents the generation of a spark discharge, in the event that there is insufficient or no contact between the sleeve and the sample under investigation which lies at the reference potential. In this manner, there may be achieved the result that a spark discharge can be generated only when the sample, the sleeve and the operating personnel are all at the same potential so that there exists no danger for the operating personnel when working with the spectrometric device.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a perspective view of a spectrometric device and schematically illustrates a sleeve and counterelectrode according to the invention;

FIG. 2 is a perspective view of the interior of the spectrometric device of FIG. 1; and FIG. 3 is a view, partially in section, illustrating an embodiment of the invention.

DESCRIPTION OF THE PREFERRED EMBODIMENTS:

Referring first to FIG. 1 of the drawing, it is pointed out that this represents a perspective view of an arrangement or device for the spectral analysis of substances as disclosed in one of the above-referenced applications by the same assignee, namely, the application Ser. No. 665,770 filed Mar. 10, 1976. The spectrometric device comprises a housing which includes an upper or cover portion 1 and a lower portion 2. The upper portion 1 and the lower portion 2 of the housing are both in the form of a segment of a circle. The housing further includes a back portion 3 which is configured as a cylindrical section as well as a pair of lateral portions 4 each of which is of platelike configuration. Only one of the lateral portions 4 of the housing is visible and this is provided with a handle 5 for carrying the device.

Referring now to FIG. 2 as well as FIG. 1, it will be seen that a concave diffraction grating 25 is mounted interiorly of the housing of the device. In addition, a carrier 32 is mounted interiorly of the housing of the device. The carrier 32 carries a slit 34 and the latter constitutes the primary slit of the device, that is, the radiation derived from a sample being investigated is directed to the grating 25 via the slit 34. A series of secondary slits 21 is provided in a carrying member 20 which is likewise arranged interiorly of the housing of the device.

An adjusting screw 13 for the carrier 32 and the primary slit 34 is provided in the visible lateral portion 4 of the housing of the device and the adjusting screw 13 extends through this lateral portion 4 of the housing. Furthermore, as best seen from FIG. 1, the arcuate back portion 3 of the housing is provided with a mounting 14 having a window 15 through which the radiation derived from a sample being investigated enters the interior of the housing. A lens 15' is arranged interiorly of the mounting 14 behind the window 15 and serves to form an image of the radiation derived from a sample being investigated on the concave grating 25 located interiorly of the housing.

The radiation from a sample being investigated is derived by means of a spark discharge. For the generation of the spark discharge, a protective housing 16 is mounted on the arcuate back portion 3 of the housing of the device. A sleeve member or sleeve 17 is, in turn, mounted on the protective housing 16. The sleeve 17, which is here composed of metal, concentrically surrounds an electrode 17', that is, a counterelectrode, which serves to generate the spark discharge. It may be seen that the sleeve 17 is provided with a semi-circular cutout or opening 17" which is directed towards the mounting 14 and the lens 15'.

By placing the spectrometric device with the sleeve 17 on a sample to be investigated, the sleeve 17 with the cutout 17" forms an exit window for the spark discharge. An image of the spark discharge is then formed on the concave grating 25 via the lens 15' by means of the exit window thus formed. The spark discharge is generated and controlled via a spark overvoltage generating device located in an apparatus 17''' which is connected with the spectrometric device by means of the high-voltage cables illustrated in FIG. 1 but not identified by a reference numeral. The sleeve 17 is a component of a protective circuit which isolates the spark overvoltage generating device located in the apparatus 17''' in the event that the electrode 17', that is, the protective sleeve 17, does not contact the sample and, at the same time, does not lie at the ground potential of the operating personnel.

A power supply, an analyzer and an overall control system which may be used with an arrangement in accordance with the invention are all subjects of different ones of the earlier-mentioned copending applications by the same assignee, namely, the applications mentioned above.

Referring again to FIG. 2, it may be seen that a supporting unit is provided interiorly of the spectrometric device. The supporting unit includes a body or base 2' and lateral profiled strips 2". The base 2' and the lateral profiled strips 2" form a distortion-resistant unitary member, namely, the supporting unit 2', 2".

The supporting unit 2', 2" is elastically suspended at three points interiorly of the actual housing of the device. The carrying member 20 which is provided with the secondary slits 21 is mounted on the supporting unit 2', 2". It may be seen that the carrying member 20 is arcuate and, more particularly, is curved so as to correspond to the curvature of the Rowland circle. Thus, the secondary slits 21, whose positions are or may be aligned in correspondence with the spectral lines of samples to be investigated, lie on a path which follows the arc of the Rowland circle. The carrying member 20 carrying the secondary slits 21 is adjustably mounted on the supporting unit 2', 2" and adjusting screws 22 and 23 are provided for the adjustment of the carrying member on the supporting unit 2', 2".

The carrying member 20 guides the carrier 32 with the primary slit 34 on which the image of the spark discharge is formed via the lens 15' indicated in FIG. 1. The concave grating 25 is mounted on a support plate which has not been illustrated here for the sake of clarity.

A heating foil 23' is provided at the bottom of the housing of the spectrometric device and enables the housing to be maintained at a higher temperature than the surroundings during operation. In this manner, variations in the temperature of the surroundings may be prevented from changing the existing temperature of the device itself and, concomitantly, thermal expansions and contractions may be avoided.

FIG. 3 shows a part of the back portion 3 of the housing of the spectrometric device and, as mentioned earlier, the back portion 3 of the housing has the form of a section of a cylinder. In particular, FIG. 3 illustrates that part of the back portion 3 of the housing of the spectrometric device on which the protective housing 16 is fastened.

An insulating body 40 is arranged interiorly of the protective housing 16. The insulating body 40, which is provided with a bore or hole, has an edge face 41. A metallic casing 42 is provided in the bore of the insulating body 40 and projects beyond the edge face 41 of the latter.

The metallic casing 42 extends from the insulating body 40 into an insulating casing 44. A clamping sleeve 45 is arranged interiorly of the insulating casing 44 and lies adjacent the metallic casing 42. The counterelectrode 17' extends into the clamping sleeve 45 and may be locked in position therein by means of an insulating screw 46 provided for this purpose.

The insulating casing 44 extends to an insulating member 47 which has a hollow cylindrical configuration. The metallic sleeve 17 is positioned over the insulating member 47. The bores of the metallic casing 42, the clamping sleeve 45, the insulating casing 44 and the insulating member 47 are aligned with one another and receive the counterelectrode 17'. A spring 48 is provided in the metallic casing 42 and serves to subject the counterelectrode 17' to a biasing action.

The spring 48, as well as the metallic casing 42, are in electrically conductive contact with a connecting plate 48'. The latter is, in turn, connected with a high-voltage cable 511 for supplying voltage to the counterelectrode 17'.

The sleeve 17 is provided with a connection of terminal 52. The terminal 52 may be connected to a protective circuit which isolates the spark overvoltage generating device, that is, which prevents the generation of a spark discharge, in the event that the sleeve 17 does not, or does not adequately, contact the sample under investigation.

FIG. 3 shows the spectrometric device arranged for the examination of a sample. The sample, which is identified by the reference numeral 50, forms the spark gap together with the counterelectrode 17'. The electrode spacing, that is, the spark gap or the distance between the counterelectrode 17' and the sample 50, is predetermined by the sleeve 17 as will be apparent.

Before operation, the insulating screw 46 is loosened. The electrode spacing is then adjusted by means of a suitable gauge which is placed at or on the edge of the sleeve 17. After adjustment of the electrode spacing, the insulating screw 46 is tightened and the electrode spacing is fixed by the sleeve 17.

By virtue of the adjusting means for the primary slit 34 and the grating 25 which is provided by the invention, as well as by virtue of the utilization of a light supporting unit 2', 2" according to the invention, it becomes possible to construct the spectrometer as a handy portable device, especially when operation is not carried out under vacuum. The device for generating the spark discharge may likewise be made portable by suitable dimensioning. Furthermore, due to the incorporation of protective or breaker circuits which prevent the generation of a spark discharge if the sample to be investigated and the casing 17 which is constructed as a safety contact are not simultaneously at ground potential, care is taken that the operating personnel are protected against the high voltages generated by the electronic auxiliary devices. The construction of a spark gap with protective circuits is the subject of another application by the same assignee, namely, the earlier-mentioned application Ser. No. 665,773 filed Mar. 10, 1976, and is accordingly not described here in further detail.

It will be understood that each of the elements described above, or two or more together, may also find a useful application in other types of constructions and operations differing from the types described above.

While the invention has been illustrated and described as embodied in a transportable device for the spectral analysis of metals, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and described to be protected by Letters Patent is set forth in the appended claims.

1. An apparatus for spectroscopically analyzing the composition of a workpiece, said apparatus comprising:
a support;

a sleeve mounted on said support and having an open end engageable with a surface of the workpiece and formed with a laterally open cutout;

an electrode on said support and having an electrode tip limitedly displaceable in said sleeve adjacent said open end thereof;

means between said support and said electrode for fixing said electrode in said sleeve with said tip spaced inwardly of said open end thereof;

means connected to said electrode for sparking between said surface and said tip when same are spaced apart and said open end abuts said surface;

optical means on said support directed through said cutout at the space between said tip and said surface and including a primary slit for transmitting into said support the light of a spark in said space between said tip and said surface; and means in said support including a Rowland grating and a plurality of secondary slits for breaking the light received from said optical means down into an analyzable spectrum.

2. The apparatus defined in claim 1 wherein said support is portable.

3. The apparatus defined in claim 1 wherein said sleeve is conductive.

4. The apparatus defined in claim 3 wherein said support includes a member of insulating material on which said sleeve is mounted.

5. The apparatus defined in claim 4 wherein said means between said support and said electrode is a screw threaded into said member and engaging said electrode.

6. The apparatus defined in claim 3, further comprising a tube of insulating material between said electrode and said sleeve, said tube being fixed relative to said sleeve.

7. The apparatus defined in claim 1 wherein said sleeve has at said open end an end face lying substantially in a plane, said tip being pointed and spaced from said plane.

8. The apparatus defined in claim 1 wherein said means for sparking is also connected to said sleeve, whereby electrical contact is made between said sleeve and said workpiece on physical engagement between said open end and said surface.

9. The apparatus defined in claim 8 wherein said means for sparking includes safety means for preventing sparking between said surface and said tip when said open end is out of electrical contact with said surface.

10. The apparatus defined in claim 1 wherein said optical means includes a lens focused through said cutout at said space.

* * * * *